United States Patent [19]

Harrison

[11] 3,968,127

[45] July 6, 1976

[54] HYDROCARBON OXIDATION PROCESS

[75] Inventor: Jonas P. Harrison, Pinole, Calif.

[73] Assignee: Chevron Research Company, San Francisco, Calif.

[22] Filed: Apr. 24, 1975

[21] Appl. No.: 571,183

[52] U.S. Cl. .......................................... 260/346.8 A
[51] Int. Cl.$^2$ ...................................... C07D 307/60
[58] Field of Search ................................ 260/346.8

[56] References Cited
FOREIGN PATENTS OR APPLICATIONS
48-19515   3/1973   Japan .............................. 260/346.8

OTHER PUBLICATIONS

Belostotskaya et al., Neftekhimiia, vol. 8, pp. 379–385, (1968).

*Primary Examiner*—Harry I. Moatz
*Attorney, Agent, or Firm*—G. F. Magdeburger; John Stoner, Jr.; T. G. DeJonghe

[57] ABSTRACT

A process for producing citraconic anhydride from isoprene which comprises contacting the isoprene feed and oxygen-containing gas in vapor phase in a pretreatment zone at a temperature between 150° and 430°C with a solid base composition, said base composition comprising an alkali or alkaline earth metal, and then contacting the effluent from the pretreatment zone at a temperature between 180° and 500°C with a hydrocarbon oxidation catalyst effective for catalyzing the reaction of isoprene with oxygen to obtain citraconic anhydride.

10 Claims, No Drawings

HYDROCARBON OXIDATION PROCESS

BACKGROUND OF THE INVENTION

The present invention relates to a process for the production of citraconic anhydride, particularly by oxidation of isoprene.

Citraconic acid anhydride is a known chemical having known uses such as a food acidulant and in preparing polymers or resins, which resins can be used in production of fiberglass reinforced plastics.

Previous methods for producing citraconic anhydride have included the distillation of citric acid. Rapid distillation of citric acid yields citraconic and itaconic anhydride. Repeated distillation of itaconic anhydride yields citraconic anhydride. See, for example, Kirk-Othmer, *Encyclopedia of Chemical Technology*, Second Edition, Volume 1, at page 253; U.S. Pat. No. 2,088,347; and U.S. Pat. No. 2,258,947.

U.S. Pat. No. 2,966,498 discloses preparation of citraconic anhydride by pyrolysis of itaconic acid in the presence of alkali metal salts.

Several patents to Kerr, namely 3,296,282; 3,255,211; 3,255,212; 3,255,213; 3,156,705; 3,156,706; 3,156,707; and 3,094,539, discloses oxidation of olefinic feeds to dicarboxylic acid anhydrides, particularly maleic anhydride. Although the Kerr patents are concerned with the oxidation of butene-2, other ethylenically unsaturated feeds are mentioned, such as 3-methylbutene-1, isoprene, 2,3-dimethyl butadiene and butadiene-1,3 and mixtures thereof. The Kerr references disclose numerous hydrocarbon oxidation catalysts, including vanadium and phosphorus mixed oxide catalyst, which catalyst may contain added alkali or alkaline earth components as disclosed, for example, in U.S. Pat. Nos. 3,255,211 and 3,255,212.

U.S. Pat. Nos. 3,478,063 and 3,538,122 to Friedrichsen et al also disclose hydrocarbon oxidation catalysts for converting unsaturated hydrocarbons to maleic anhydride.

U.S. Pat. No. 2,719,853 discloses the catalytic production of citraconic acid by oxidation of a hydrocarbon. According to this patent, the catalyst used in a vanadium oxide catalyst promoted with arsenic. The hydrocarbon feed used in the examples of this patent was a cracked naphtha containing $C_4$–$C_6^+$ hydrocarbons, including paraffins and olefins. No iso-$C_5$ olefins were disclosed as present in the feed, and the feed was evidently passed directly over the vanadium arsenate catalyst at 900°F with no pretreatment.

SUMMARY OF THE INVENTION

According to the present invention a process is provided for producing citraconic acids and/or anhydride from isoprene, which process comprises contacting the isoprene feed and oxygen-containing gas in vapor phase in a pretreatment zone at a temperature between 150° and 430°C with a solid base composition, said base composition comprising an alkali or alkaline earth metal, and then contacting the effluent from the pretreatment zone at a temperature between 180° and 500°C with a hydrocarbon oxidation catalyst effective for catalyzing the reaction of isoprene with oxygen to obtain citraconic anhydride.

Among other factors, the present invention is based on my finding that pretreatment of the isoprene feed in accordance with the present invention surprisingly increases the yield of citraconic anhydride from isoprene. Improved yields of citraconic from 3-methyl-3-buten-1-ol can also be obtained using the process of the present invention, which embraces the pretreatment step, as opposed to a similar process but with no pretreatment step.

Suitable hydrocarbon oxidation catalysts include those effective for production of phthalic anhydride or maleic anhydride by oxidation of hydrocarbon feeds such as oxylene, benzene and butene. Thus, suitable hydrocarbon oxidation catalysts include those wherein the catalyst comprises an oxide or mixed oxide of vanadium, chromium, or molybdenum; or a mixed oxide of tin and antimony, vanadium and chromium, tin and molybdenum, molybdenum and phosphorus, vanadium and phosphorus, vanadium and arsenic, or vanadium and titanium.

Preferably the hydrocarbon oxidation catalyst comprises an oxide of vanadium and phthalic anhydride catalysts such as those comprising vanadium oxide, titanium oxide, and an alkali metal are especially preferred. Thus, a preferred hydrocarbon oxidation catalyst comprises $V_2O_5$, $K_2SO_4$, and $TiO_2$.

The hydrocarbon oxidation catalyst can be supported, for example, on a porous support such as silica, alumina, or mixtures of silica and alumina. Preferred and particularly preferred operating conditions for the process of the present invention include the following:

| Pretreatment Zone | Preferred | More Preferred |
|---|---|---|
| Temperature, °C | 150–430 | 190–260 |
| Pressure, psig | 0–50 | 0–30 |
| Space Velocity, VVH | 2000–7500 | 4000–6000 |
| Vol % Isoprene in Air | .25–3 | .25–1.5 |

| Hydrocabon Oxidation Zone | Preferred | More Preferred |
|---|---|---|
| Temperature, °C | 180–500 | 200–400 |
| Pressure, psig | 0–50 | 0–30 |
| Space Velocity, VVH | 2000–7500 | 4000–6000 |
| Vol % Isoprene in Air | .25–3 | .25–1.5 |

VVH = Vol. of Isoprene in Air feed gas per vol. catalyst per hour.

The pretreatment zone can be in a reactor or vessel separate from the reactor or vessel wherein the isoprene is oxidized to citraconic anhydride. Also the pretreatment zone can be in a common reactor, but in any case the pretreatment zone comprises a separate or discrete bed of catalyst prior to the hydrocarbon oxidation zone or the catalyst bed. Preferably the pretreatment zone is immediately before the oxidation zone and in the same reactor.

Typically the solid composition or catalyst used in the pretreatment zone is essentially free of vanadium oxide, molybdenum oxide, or other of the common hydrocarbon oxidation components, exclusive of basic acting components — that is, alkali or alkaline earth metal components — and exclusive of support components. Thus, the essential ingredient of the pretreatment zone composition is a basic acting component, particularly an alkali or alkaline earth metal component such as lithium, sodium, potassium, rubidium, cesium, and francium; and beryllium, magnesium, calcium, strontium, barium and radium. Of these alkali and alkaline earth metal components lithium, sodium and potassium are particularly preferred, with potassium being the most preferred. The basic acting component can be in compound form, such as oxides, or salts, such as sulfates.

The alkali or alkaline earth metal preferably is supported on a support material; preferred support materials comprise silica or alumina or an inert support e.g., silicon carbide. Silica is particularly preferred as the support material.

EXAMPLES

Example 1: Preparation of the pretreatment solid base composition

A potassium base catalyst was prepared by adding 22.7 grams of a potassium sulfate solution (0.62 grams of $K_2SO_4$ per 100 grams water) to 14.12 grams of silica (Davison high-porosity silica gel). After soaking for 1 hour, the silica was dried in air at 150°C for 16 hours. The dried catalyst was calcined by heating at 500°C for 3 hours. Analysis of the calcined catalyst showed 1 weight percent $K_2SO_4$ based on silica.

Example 2: Preparation of a vanadium-containing oxidation catalyst

A vanadium-on-silica catalyst was prepared by adding 112 grams of $V_2O_5$ in 1 liter of water containing 372 grams of oxalic acid. The mixture was heated to 100°C to insure complete reaction of the $V_2O_5$. After cooling the solution weighed 1,213 grams. To 19.5 grams of this solution was added 0.087 grams of $K_2SO_4$. The resulting solution was mixed with 15 grams of silica (see Example 1), and allowed to stand for 16 hours at ambient temperature. Then it was heated to 150°C and dried in air. This catalyst was activated by heating it in a gas stream containing 1½% butane-in-air for 16 hours at 480°C. Analysis showed the catalyst to consist of 12% $V_2O_5$, 0.6% $K_2SO_4$, and 87.4% of $SiO_2$ (weight percent).

Example 3: Preparation of citraconic acid over the oxidation catalyst of Ex. 2.

A ½ inch internal diameter electrically heated tubular reactor was charged with about 5 cc of the catalyst of Example 2. Quartz, about 5 cc each, was placed above and below this catalyst bed. Isoprene, 1.33 mole percent in air, was charged to the reactor at a variety of conditions. Maximum yield was obtained at a feed rate of 5000 v/v/hr to the reactor at 226°C. After 50 hours on stream, the gaseous products were analyzed and found to contain 15.7 moles citraconic acid, 4.2 moles maleic anhydride, 4.1 moles acrylic acid, 12 moles acetic acid, 180 moles carbon monoxide and 200 moles of carbon dioxide per 100 moles of isoprene feed.

Example 4: Preparation of citraconic acid over the catalyst of Example 2 preceded by the base component of Example 1

Example 3 was repeated, except the quartz preceding the acidation catalyst was replaced by the solid base composition prepared in Example 2. In this case, maximum yield was obtained at 3300 v/v/hr and a reactor temperature of 256°C. The yield of citraconic acid was 22 moles per 100 moles of isoprene feed. By-products were 16 moles of acetic acid, 3 moles of acrylic acid, 2 moles of maleic acid, 157 moles of CO and 183 moles of $CO_2$.

A comparison of Examples 3 and 4 shows that a solid base composition preceding an oxidation catalyst increased the yields of citraconic acid by about 25%, and significantly reduced the quantities of by-products.

Example 5: Preparation of citraconic acid over a commercial oxidation catalyst preceded by the base component of Example 1

The reactor was loaded as in Example 4, except that the oxidation catalyst was replaced by a commercial phthalic anhydride catalyst containing 5% (wt.) vanadium oxide and 32% (wt.) $K_2SO_4$ on a $TiO_2$ support. Isoprene and air were charged at 4800 v/v/hr under a variety of conditions as shown in Table I.

This example shows that yields approaching 50 mole percent are possible utilizing the process of this invention.

TABLE I

| | | | Citraconic Acid from Oxidation of Isoprene Moles of Product per 100 Moles of Isoprene | | | | | |
|---|---|---|---|---|---|---|---|---|
| Example | Isoprene Mole % | Temp. °C | Citraconic Acid | Acetic Acid | Acrylic Acid | Maleic Acid | CO | $CO_2$ |
| 5a | 1.0 | 350 | 22 | 12 | 15 | 3 | 25 | 57 |
| 5b | 0.28 | 351 | 48 | 31 | 7 | 10 | — | — |
| 5c | 0.28 | 363 | 43 | 23 | 17 | 6 | 7 | 30 |

What is claimed is:

1. A process for producing citraconic anhydride from isoprene which comprises contacting the isoprene feed and oxygen-containing gas in vapor phase in a pretreatment zone at a temperature between 150° and 430°C with a solid base composition, said base composition consisting essentially of an alkali or alkaline earth metal, and then contacting the effluent from the pretreatment zone at a temperature between 180° and 500°C with a hydrocarbon oxidation catalyst effective for catalyzing the reaction of isoprene with oxygen to obtain citraconic anhydride, wherein the hydrocarbon oxidation catalyst consists essentially of an oxide of vanadium, chromium, molybdenum, or a mixed oxide of tin and antimony, vanadium and chromium, tin and molybdenum, molybdenum and phosphorus, vanadium and phosphorus, vanadium and arsenic, or vanadium and titanium, and wherein the base composition and hydrocarbon catalyst are discrete catalyst beds.

2. A process in accordance with claim 1 wherein the hydrocarbon oxidation catalyst consists essentially of an oxide of vanadium.

3. A process in accordance with claim 1 wherein the hydrocarbon oxidation catalyst consists essentially of vanadium oxide, titanium oxide and an alkali metal.

4. A process in accordance with claim 1 wherein the hydrocarbon oxidation catalyst consists essentially of $V_2O_5$, $K_2SO_4$ and $TiO_2$.

5. A process in accordance with claim 1 wherein the base composition is disposed on a support.

6. A process in accordance with claim 2 wherein the base composition is disposed on a support.

7. A process in accordance with claim 6 wherein the support comprises silica or alumina.

8. A process in accordance with claim 6 wherein the support is silica.

9. A process in accordance with claim 1 wherein the hydrocarbon oxidation catalyst is disposed on a support.

10. A process in accordance with claim 9 wherein the support is silica, alumina, or mixtures thereof.

* * * * *